United States Patent [19]

Takasaki et al.

[11] Patent Number: 4,584,197

[45] Date of Patent: Apr. 22, 1986

[54] PROCESS FOR PREPARATION OF FISH AND SHELLFISH EXTRACTS HAVING PHARMACEUTICAL FUNCTIONS

[75] Inventors: Takashi Takasaki; Mitsunori Iwamoto, both of Karatsu, Japan

[73] Assignee: Nihon Bussan Kabushiki Kaisha, Karatsu, Japan

[21] Appl. No.: 492,079

[22] Filed: May 6, 1983

[30] Foreign Application Priority Data

Mar. 4, 1983 [JP] Japan ................................. 58-34385

[51] Int. Cl.$^4$ ...................... A61K 35/60; C12P 21/00; C07G 17/00
[52] U.S. Cl. ........................................ 424/95; 435/68; 435/267; 435/268
[58] Field of Search ....................... 435/267, 268, 68; 424/95

[56] References Cited

U.S. PATENT DOCUMENTS 4,036,993 7/1977 Ikeda et al. ..................... 435/267

Primary Examiner—Sam Rosen
Attorney, Agent, or Firm—Jordan and Hamburg

[57] ABSTRACT

A process for the preparation of fish and/or shellfish extracts having various pharmaceutical functions is provided. The process comprises decomposing raw fish and/or shellfish at a pH of 6.0 to 7.0 with a *Bacillus subtilis* derived proteinase and decomposing at the same pH range with a Koji mould derived proteinase. The product extracts contain peptide amino acids each having a molecular weight of substantially less than 3000 and free amino acids. According to the invention, medicines containing the fish and/or shellfish extracts are also provided such as nutrition balancing medicines, anti-ulcer medicines, diabetes relieving medicines, antilipemic medicines and rheumatism and arthritis relieving medicines.

3 Claims, 7 Drawing Figures

PROCESS FOR PREPARATION OF FISH AND SHELLFISH EXTRACTS HAVING PHARMACEUTICAL FUNCTIONS

BACKGROUND OF THE INVENTION

1. Field of the Invention;

The present invention relates to a process for the preparation of fish and/or shellfish extracts having pharmaceutical functions and medicines containing the fish and/or shellfish extracts prepared thereby. More particularly, the invention relates to a process for the preparation of fish and/or shellfish extracts having nutrition balancing function, anti-ulcer function, insulin-like function, antilipemic function, and the function of relieving rheumatism and arthritis, and also relates to medicines containing the fish and shellfish extracts prepared by the above process.

2. Prior Art;

One of the known processes for the extraction of fish meat extracts is disclosed in Japanese Patent Publication No. 31935/1978. In this process, raw fishes which have not been subjected to pre-treatment, such as slicing or grinding to form a slurry, are heated to a temperature of not lower than 60° C. followed by decomposition by the use of an alkali-resistant proteinase at 50° to 60° C. and at a pH of 9 to 10, and then the decomposed products are further decomposed using a different acid-resistant proteinase after adjusting the pH value to pH 5 to 6. However, this known process has a disadvantage that the pH value of the raw material must be adjusted to pH 9 to 10 by the addition of a sodium ion containing compound, such as sodium carbonate, which is disagreeable from the food sanitary standpoint of view, in order to activate the alkali-resistant proteinase. In addition, this known process involves a cumbersome and difficult pH adjusting operation, since the reaction product must be adjusted to have a pH of 5 to 6 prior to the addition of an acid-resistant proteinase. Another disadvantage of this known process is that the alkali-resistant proteinase is not fully deactivated to continue its action after the acid-resistant proteinase is added to make it difficult to prepare the extract containing only the peptides each having a molecular weight of substantially less than 3000 and free amino acids.

OBJECTS AND SUMMARY OF THE INVENTION

A primary object of this invention is to provide a process for the preparation of fish and/or shellfish extracts having pharmaceutical functions and mainly composed of peptides each having a molecular weight of substantially less than 3000 and free amino acids, and to provide medicines containing the thus prepared fish and/or shellfish extracts.

Another object of this invention is to provide a process for the preparation of fish and/or shellfish extracts, wherein delicate pH adjusting operation is eliminated, and to provide medicines containing the thus prepared fish and/or shellfish extracts.

A further object of this invention is to provide a process for the preparation of fish and/or shellfish extracts having nutrition balancing function; and to provide a medicine for promoting nutrition and containing the thus prepared fish and/or shellfish extracts.

Laboratory tests shown herein indicate that the extracts of the invention have anti-ulcer activity, insulin-like activity, antilipemic function, cholesterol lowering activity, and activity in treating rheumatism and arthritis.

A still further object of this invention is to provide a process for the preparation of fish and/or shellfish extracts having anti-ulcer function, and to provide an anti-ulcer medicine containing the thus prepared fish and/or shellfish extracts.

A further object of this invention is to provide a process for the preparation of fish and/or shellfish extracts having insulin-like function, and to provide a medicine for relieving diabetes containing the thus prepared fish and/or shellfish extracts.

A further object of this invention is to provide a process for the preparation of fish and/or shellfish extracts having antilipemic function, and to provide a medicine for lowering cholesterol content in blood and containing the thus prepared fish and/or shellfish extracts.

A further object of this invention is to provide a process for the preparation of fish and/or shellfish extracts having a function of relieving rheumatism and arthritis, and to provide a medicine for relieving rheumatism and arthritis containing the thus prepared fish and/or shellfish extracts.

The above and other objects of this invention will become apparent from the following description of the invention.

In accordance with the present invention, there is provided a process for the preparation of fish and/or shellfish extracts having pharmaceutical functions, which comprises the steps of heating uncomminuted raw fish and/or shellfish to a temperature of not lower than 75° C. to fully deactivate autolysis enzymes contained in said raw fish and/or shellfish and simultaneously to remove fish smell, adding a Bacillus subtilis derived proteinase to said fish and/or shellfish at a temperature of from 50° to 60° C. and at a pH of from 6.0 to 7.0 to decompose the proteins contained in said fish and/or shellfish to the stage of proteoses, raising the temperature to not lower than 75° C. to fully deactivate said Bacillus subtilis derived proteinase, adding a Koji mould derived proteinase to said proteoses derived from said fish and/or shellfish at a temperature of from 40° to 50° C. and at a pH of from 6.0 to 7.0 and maintaining the mixture at said temperature for 1 to 3 hours to decompose said proteoses into peptides having a molecular weight of substantially less than 3000 and free amino acids, raising the temperature to not lower than 75° C. to fully deactivate said Koji mould derived proteinase, and separating and then concentrating the resultant decomposition products.

It is to be understood here and throughout the specification and claims that it is proteinase produced by a Bacillus subtilis which decomposes the proteins contained in the fish and/or shellfish to the stage of proteoses and this is the sense in which the term "Bacillus subtilis derived proteinase" is used and that it is proteinase produded by a Koji mould which decomposes the aforementioned proteoses into peptide amino acids each having a molecular weight of substantially less than 3000 and free amino acids and this is the sense in which the term "Koji mould derived proteinase" is used.

According to a further aspect of this invention, there is provided a variety of medicines containing the fish and/or shellfish extracts prepared by the aforementioned process and having various pharmaceutical functions.

DESCRIPTION OF THE INVENTION

Figure 1:
FIG. 1 is a photograph showing the lungs of a porker dosed with the mackerel extract prepared by the process of the invention and the lungs of a control porker which is not dosed with the extract.

The present invention will be described in detail hereinbelow. The inventors have studied a process for the preparation of fish and/or shellfish extracts comprising the steps of decomposing a variety of fish and/or shellfish at a pH of 6.0 to 7.0 and at a temperature of 50° to 60° C. by the action of a Bacillus subtilis derived proteinase, completely deactivating the Bacillus subtilis derived proteinase, and then decomposing the products derived from said fish and/or shellfish by the action of a Koji mold derived proteinase at a pH of 6.0 to 7.0 and at a temperature of 40° to 50° C. for 1 to 3 hours. As a result, we have found that fish and/or shellfish extracts mainly composed of peptides having a molecular weight of substantially less than 3000 and free amino acids can be obtained by the above process and that the fish and/or shellfish extracts prepared through the aforementioned process have various pharmaceutical functions since the whole bodies of fish and/or shellfish including internal organs are decomposed by the process. It is further found that the fish and/or shellfish extracts prepared through the process of the invention and having the peculiar amino acids composition as aforementioned, namely the proteins contained in the raw fish and/or shellfish being decomposed to form a composition mainly composed of peptides having a molecular weight of substantially less than 3000 and free amino acids, exhibit nutrition balancing function, anti-ulcer function, insulin-like function, antilipemic function and the function of relieving rheumatism and arthritis.

In the process of the invention, the whole bodies of raw fish and/or shellfish, such as saurel, mackerel, sardine, mackerel pike, tuna, Atkamackerel, cod, cuttlefish, octopus, shrimp, prawn, oyster, corbicula, short-necked clam, hard-shelled mussel, species of ark shell and clam, are charged in a reaction vessel without subjecting to any pre-treatment, such as slicing or grinding to form a slurry. Large size materials may be cut to have appropriate dimensions. Immediately after charging into the reaction vessel, the temperature of the charged fish and/or shellfish is raised to not lower than 75° C., preferably not lower than 80° C., to fully deactivate the autolysis enzymes contained in the raw fish and/or shellfish and simultaneously to remove the fish smell or bad odor emitted from the products of autolysis. The content in the reaction vessel may be maintained at the raised temperature generally from about 10 minutes to about one hour to deactivate the autolysis enzymes. In the prior art process referred to hereinbefore, the lowest temperature for deactivation of autolysis enzymes is 60° C. However, in the process of this invention for preparing fish and/or shellfish extracts having pharmaceutical functions, the lowest temperature for deactivation of autolysis enzymes should be not lower than 75° C. in order to remove fishy smell or bad odor completely.

Then, the proteins contained in the fishes and/or shellfishes are decomposed to the stage of proteoses at a temperature of from 50° to 60° C. and at a pH of 6.0 to 7.0, preferably 6.0 to 6.5, by the addition of a Bacillus subtilis derived proteinase. A preferred enzyme for use in this step is a fish-soluble enzyme manufactured in Japan by Kinki Yakuruto Manufacturing Co., Ltd. and sold through Yakuruto Biochemistry Co., Ltd., as sales agent, under the trademark "AROAZE AP-10", and this enzyme is used in the following Examples. The time period for this decomposition step is not critical, and generally ranges from 1 to 3 hours, preferably 1.5 to 2 hours. In the process of this invention, the pH adjusting operation is not required since this decomposition step is carried out at a pH of 6.0 to 7.0 ranging within neutral or weakly acidic range, and the swelling of the muscle meats of the raw fishes and/or shellfishes and the separation thereof from the bones are not appreciable when compared to the process in which the first decomposition step is carried out in the alkaline pH range. By continuing decomposition at the pH range as defined in the claims, namely at a pH of 6.0 to 7.0, the proteins are fully decomposed to the stage of proteoses without producing low molecular weight peptides and free amino acids. It is essential that the proteins be fully decomposed to the stage of proteoses at this step to provide a mixture mainly composed of proteoses which are well adapted to be decomposed by the enzymatic decomposition at the subsequent step.

Then, the temperature of the content in the reaction vessel is raised to 75° C. at the lowest, preferably to a temperature of not lower than 80° C. During this step at which the content in the reaction vessel is maintained at the raised temperature, the Bacillus subtilis derived proteinase used in the preceding decomposition step is fully deactivated. For this purpose, the content in the reaction vessel is maintained at the deactivation temperature generally for 10 minutes to one hour, preferably 15 to 30 minutes. If this deactivation step is omitted, the proteinase used in the preceding decomposition step continues its action on the content in the vessel during the subsequent enzymatic decomposition step, resulting in failure in preparation of fish and/or shellfish extracts containing a specific composition of amino acids and having various pharmaceutical functions, and the objects of this invention cannot be attained.

The subsequent step of the process of this invention is the enzymatic decomposition step carried out at a temperature of 40° to 50° C. and at a pH of 6.0 to 7.0 by the addition of a Koji mould derived proteinase. There is no need to adjust the pH value of the content in the reaction vessel prior to this step. A particularly useful enzyme for use in this step is manufactured in Japan by Kinki Yakuruto Manufacturing Co., Ltd. and sold through Yakuruto Biochemistry Co., Ltd., as sales agent, under the trademark "PUNCHDAZE". Since the Bacillus subtilis derived proteinase has been fully deactivated prior to this step, only the Koji mould producing proteinase acts on the proteoses produced by the preceding decomposition step to decompose the same into peptides having a molecular weight of substantially less than 3000 and into free amino acids. Time period for this decomposition step ranges 1 to 3 hours, preferably about 2 hours. Since the decomposition step is carried out under more moderate conditions as compared to the conditions of the prior art process, namely at a lower temperature within a pH range of weakly acidic or neutral zone, the aimed particular composition of amino acids can be obtained. If the time period of this decomposition step is less than one hour, some portions of proteoses are left to result in failure in obtaining the aimed particular composition of amino acids. On the contrary, if the time period of this decomposition step exceeds 3 hours, the pharmaceutical functions of the product are adversely affected.

Immediately after the decomposition step, the temperature of the content in the reaction vessel is raised to not lower than 75° C., preferably not lower than 80° C., to fully deactivate the Koji mould derived proteinase in order to prevent further action of the proteinase causing deterioration of the product and to prevent the pharmaceutical functions of the product from being lowered.

The decomposed products are then separated, by means of ordinary methods using a centrifugal separator or other known devices, into a fish and/or shellfish extract layer, an oil layer and a residue including bone pieces and undecomposed materials. The fish and/or shellfish extract may then be filtered and concentrated under reduced pressure at a temperature of not higher than 60° C.

The fish and/or shellfish extracts obtained through the process of the invention contain a variety of peptides and free amino acids including glutamic acid, aspartic acid, lysine, alginine, glycine, alanine, leucine, proline, histidine, phenyl alanine, serine, etc. and the peptides are mainly composed of those each having a molecular weight of substantially less than 3000. According to the present invention, fish and/or shellfish extracts containing about 30% by weight of water, more than 50% by weight, for example about 60% by weight, of crude proteins and not more than 1% by weight of crude fats can be prepared, and the extracts prepared by the process of the invention have various pharmaceutical functions as will be described in detail in the Examples gived below.

EXAMPLES OF THE INVENTION

The present invention will be described in detail by referring to some Examples thereof. Throughout the following Examples, "%" stands for "% by weight", unless otherwise specified.

EXAMPLE 1

PREPARATION OF FISH EXTRACT

Whole bodies of 4 tons of mackerel (referred to as Saba in the Tables and Figures) were, without subjecting to any pre-treatment, charged into reaction vessel provided with an agitator together with 4 tons of water, and the content of the vessel was heated to 80° C. After 15 minutes, the temperature of the content in the vessel was lowered to 55° C., and added with 4 kg of a Bacillus subtilis derived proteinase to be subjected to reaction at pH 6.2 for 1.5 hours. Then, the temperature of the content in the vessel was raised to 80° C. and maintained at that temperature for 15 minutes, followed by cooling to 45° C. at which 2 kg of a Koji mould derived proteinase was added and maintained at that temperature for 2 hours to react the content at pH 6.5.

Then, the content in the vessel was heated again to 80° C. to deactivate the proteinase. The reaction product was separated by a normal method using a centrifugal separator into an extract layer, an oil layer and a residue containing bone pieces and unreacted materials. The extract layer was filtered and concentrated under reduced pressure at 60° C. to obtain a mackerel extract or Saba extract.

The mackerel extract was analysed to reveal that it contained 35.4% of water, 57.4% of crude proteins, 0.4% of crude fats, 0.5% of carbohydrates and 6.3% of ash content, and that it had a calorie of 235 calories/g. The chromatographical analysis thereof showed that the molecular weights had three peaks at 2500, 1300 and 760 to indicate that the molecular weight of the amino acid components were substantially less than 3000. The composition of grouped amino acids and free amino acids are shown in Table 1.

TABLE 1

| Grouped Amino Acids and Free Amino Acids Contained in the Composition (g/100 g) | | | |
|---|---|---|---|
| Arginine: | 3.40 | Alanine: | 3.62 |
| Lysine: | 4.37 | Glycine: | 4.37 |
| Histidine: | 2.76 | Proline: | 2.53 |
| Phenyl Alanine: | 1.44 | Glutamic Acid: | 7.46 |
| Tyrosine: | 1.27 | Serine: | 2.24 |
| Leucine: | 3.31 | Threonine: | 2.14 |
| Isoleucine: | 1.70 | Aspertic Acid: | 4.43 |
| Methionine: | 1.23 | Triptophane: | 0.31 |
| Valine: | 2.38 | Systeine: | 0.27 |

EXAMPLE 2

NUTRITION BALANCING FUNCTION

The mackerel extract prepared in Example 1 was diluted with water by 30 times, and 10 cc of diluted extract was dosed to porkers every day after the weaning period by mixing the same into a feed, and the porkers were killed after feeding for 6 months and subjected to comparison with porkers which were not dosed with the extract.

The results of anatomical observation are shown in Table 2.

TABLE 2

| | |
|---|---|
| Lungs | Better than those of the other porkers (without dosing the extract) having clear color and having no diseased focus. (See Note 1) |
| Heart | Better than those of the other porkers (without dosing the extract) with outer walls having no adhering fats. (See Note 2) |
| Liver | The livers of the porkers dosed with the extract had no diseased focus or removed portion, and had beautiful brown color. (See Note 3) |
| Large and Small | Little fat surrounded the intestines of the porkers dosed with the extract. |

TABLE 2-continued

| Intestines Carcass | The meats of the porkers dosed with the extract had good shapes, and thick masses adhered with appropriate fats. The meats of the porkers dosed with the extract were dense and had good texture and color, with fats of good color. |
|---|---|

When compared to ordinary porkers (without dosing the extract), clear distinctions were observed in that the amounts of fats adhering to the organs were decreased and in that no diseased or removed portions were observed.

Note 1: The lungs of the porkers are shown by the photographs in FIG. 1, wherein A shows the lungs of a porker dosed with the mackerel extract according to this invention and B shows the lungs of a porker without dosing the extract. As shown, A has clear color and has no diseased focus, whereas B has dim color and has a diseased focus 1.

Figure 2:
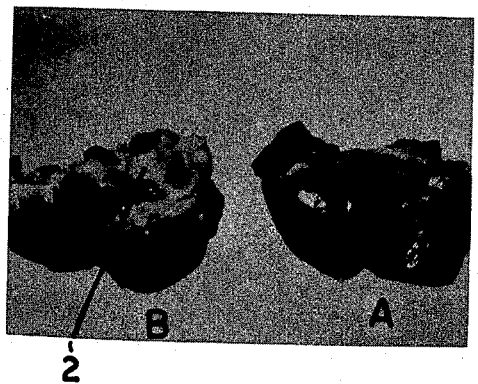
FIG. 2 is a photograph showing the heart of a porker dosed with the mackerel extract prepared by the process of the invention and the heart of a control porker which is not dosed with the extract.

Note 2: The hearts of the porkers are shown by the photographs in FIG. 2, wherein A shows the heart of a porker dosed with the mackerel extract according to this invention and B shows the heart of a porker without dosing the extract. As shown, the heart A has no adhering fats, whereas the heart B has a large quantity of fats 2.

Figure 3:
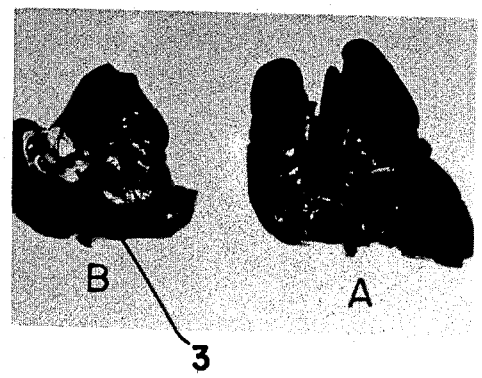
FIG. 3 is a photograph showing the liver of a porker dosed with the mackerel extract prepared by the process of the invention and the liver of a control porker which is not dosed with the extract.
Figure 4:
FIG. 4 is a photograph showing another sliced specimen of the liver of the control porker shown in FIG. 3.

Note 3: The livers of the porkers are shown by the photographs in FIGS. 3 and 4, wherein the liver A in FIG. 3 shows the liver of a porker dosed with the mackerel extract according to this invention, and B in FIG. 3 shows the liver of a porker without dosing the extract. The liver A has no diseased focus, whereas the liver B has a diseased focus 3. FIG. 4 is a photograph of a sliced specimen of the liver of the porker shown by B in FIG. 3, from which it will be seen that the diseased focus 4 extends deeply in the internal area.

EXAMPLE 3

ANTI-ULCER FUNCTION

Using the mackerel extract obtained in Example 1, the anti-ulcer function of the mackerel extract was tested utilizing the Shay Ulcer, which is one of the ulcer formation model using rats. The influence of the dosage of the extract on the gastric juice secretion was tested through the pyloric ligation method.

Test Methods (1) Anti-ulcer Function (Pyloric Ligation Ulcer)

Wistar family male rats each having a body weight of 150 to 200 grams were subjected to fasting for 24 hours, and then the pyloric regions thereof were ligated generally in accordance with the Shay et al method (see Note (1)) under etherization.

Note (1); H. Shay, S. A. Kowarov, S. S. Fels, D. Meranze, M. Gruentein and M. Siplet, Gastroenterology, 5 43 (1945)

After allowing the rats to stand for 12 hours without feeding any food and water, the stomachs of the rats were removed and the ulcers each developed at the front stomach region were indicated by the ulcer indices in accordance with the Narumi et al. method (see Note (2)).

Note (2): S. Narumi, T. Hirata, K. Gomaibashi and M. Kanno, J. Takeda Res. Lab., 29, 85 (1970)

The tested rats each had been dosed with 500 mg/kg of the mackerel extract dissolved in water through the mouth at the time of one hour before the pyloric ligation.

(2) Activity for Inhibiting Gastric Juice Secretion

The activity was determined generally in accordance with the Shay et al method. In detail, Wistar family male rats (Body Weight: 150 to 200 grams) were subjected to fasting for 48 hours, and then the pyloric regions thereof was ligated. After 4 hours, the gastric juice stored in the stomachs was picked up, and the gastric volume, total acid output and total peptic activity thereof were measured, respectively.

The total acid output was determined by the titration of a 0.02 N-NaOH using phenolphthalein as the indicator, and the total peptic activity was determined generally in accordance with the Anson method (see Note (3)) while using casein as the base material.

Note (3): M. L. Anson, J. Gen. Physiol., 22, 79 (1938)

The tested rats each were dosed with the extract through the mouth one hour before the pyloric ligation.

The details and results of the aforementioned tests are shown in Table 3.

TABLE 3

| Treatment (p.o.) | Dose (mg/kg) | No. of rats | Ulcer index (mean ± s.e.) | Gastric volume (ml/100 g b.w.) | Total acid output ($\mu$Eq/100 g b.w.) | Total peptic activity (mg as tyrosine /100 g b.w.) |
|---|---|---|---|---|---|---|
| Control[a] | — | 8 | 3.13 ± 0.55 | 4.24 ± 0.36 | 470.8 ± 42.5 | 217.7 ± 38.2 |
| Saba extract | 500 | 8 | 2.63 ± 0.46 | 2.75 ± 0.50** | 303.9 ± 76.1** | 157.3 ± 43.6 |
| Atropine | 10 | 8 | 0.00 ± 0.00* | 0.62 ± 0.18*** | 3.7 ± 17.1*** | 23.6 ± 7.4*** |

Figure 5:
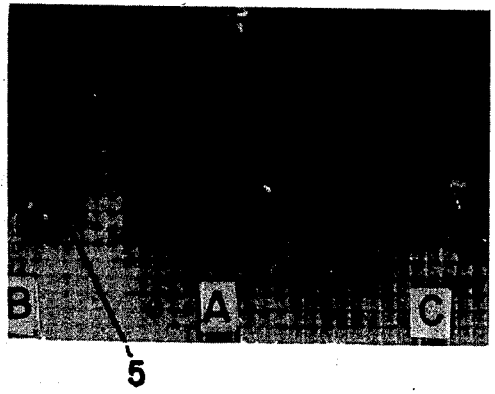
FIG. 5 is a photograph showing the stomach of a rat dosed with the mackerel extract prepared by the process of the invention and the stomachs of control rats which are not dosed with the extract.

[a]0.2% C.M.C. (carboxymethyl cellulose) in water
Significantly different from the control group:
*$p < 0.001$
**$p < 0.05$
***$p < 0.001$ As will be clearly seen from Table 3, significant differences in inhibition of gastric volume and total acid output are observed and the intention of inhibiting the formation of ulcer is recognized when the mackerel extract prepared by the process of the invention was dosed in an amount of 500 mg/kg. FIG. 5 is a photograph showing the stomachs of the rats subjected to the test experiments described in detail hereinbefore in this Example, wherein A shows the stomach of the rat dosed with the mackerel extract prepared by the process of the invention, B shows the stomach of the rat (control) without dosing the extract, and C shows the stomach of the rat dosed with astropine sulfate. As will be apparent from FIG. 5, the sliced stomachs denoted by A and C are transparent and have no ulcers, whereas the sliced stomach denoted by B has ulcerated at the portion 5.

EXAMPLE 4

INSULIN-LIKE FUNCTION

Using the mackerel extract prepared in Example 1, the insulin-like function of the extract was tested while utilizing, as the index, the effect of mackerel extract on adrenaline-induced lipolysis of the free fat cells.

Test Method

The epididymis organizatin of each rat was taken out, and the fat cells prepared through the collagenase treatment were used to learn the effect of inhibiting emission of free fatty acids from the fat cells induced by the lipolysis due to the presence of adrenaline. The results of the tests are shown in FIG. 6.

Test Results

Figure 6:
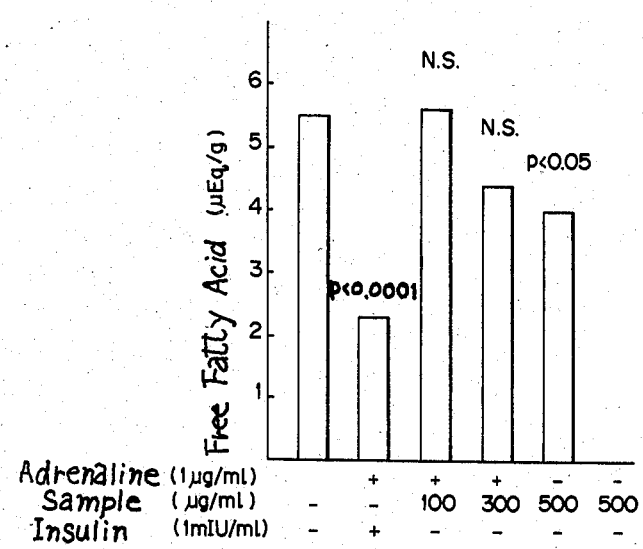
FIG. 6 is a graph showing the insulin-like function of the mackerel extract prepared by the process of the invention, in which the amounts of free fatty acids discharged from fat cells are shown.

As shown in FIG. 6, 5.5 μEq/ml of free fatty acids were isolated when 1 μg/ml of adrenaline was added to the free fat cells. The amount of the isolated free fatty acids was reduced to 2.3 μEq/g, when 1 mIU/ml of insulin was added thereto.

When the mackerel extract was used in place of insulin, an appreciable effect for inhibiting isolation of free fatty acids was observed when the concentration of the mackerel extract present in the tested system was increased to 500 μg/ml.

It should be understood, from the results set forth in FIG. 6 and described above, that the mackerel extract prepared by the process of the invention has an insulin-like function and may be used as an efficaceous medicine for curing diabetes.

EXAMPLE 5

CHOLESTEROL-LOWERING FUNCTION

The phamaceutical efficacies of the mackerel extract prepared in Example 1, when used for lowering the cholesterol content in blood or for curing slight liver defect in case of high fat feeding, were tested.

Test Method

A salad oil was heated at 170° to 180° C. for 2 hours while bubbling oxygen therethrough, whereby peroxidated fats were formed. A mixed feed was prepared by mixing a powder feed materials containing sodium cholesterol cholate with the salad oil containing peroxidated fats, and the mixed feed was fed to a group of rats. After 5 weeks, the rats caught high cholesterol disease and slight liver defects.

One group of rats was dosed with the mackerel extract to learn the cholesterol-lowering function of the extract hematologically. The internal organs of the rats were observed from the standpoint of pathological-morphorogical view. The extract was dosed to each rat one time a day through the mouth.

Test Results

Details and results of the test are shown in Tables 4 and 5. As will be clear from Tables 4 and 5, a significant effect for lowering the free fatty acids derived from neutral fats indicating the high cholesterol disease is recognized when 500 mg/kg of the mackerel extract is added. Also the GOT value of the group dosed with the extract shows significant reduction, the GOT value indicating liver diseases. The pathological-morphorogical observation of the livers revealed that the groups fed with peroxidated salad oil had a number of dead cells, and that the number of dead cells of the rats of the group dosed with the mackerel extract was decreased.

TABLE 4

Effect of Saba ext. on peroxidation of salad oil

| Treatment (p.o.) | Dose (mg/kg) | No. of rats | GOT | GPT | ALP | LDH | Total bilirubin | Direct bilirubin | Cholesterol |
|---|---|---|---|---|---|---|---|---|---|
| normal | | 7 | 88 ± 5 | 26 ± 2 | 13.2 ± 1.0 | 252 ± 65 | 0.3 ± 0 | 0.1 ± 0 | 40 ± 3 |
| control | | 7 | 93 ± 6 | 39 ± 5 | 19.2 ± 1.8 | 359 ± 58 | 0.3 ± 0 | 0.1 ± 0 | 55 ± 3 |
| Saba ext. | 200 | 7 | 94 ± 2 | 38 ± 3 | 17.6 ± 1.6 | 398 ± 68 | 0.3 ± 0 | 0.1 ± 0 | 56 ± 4 |
| Saba ext. | 500 | 7 | 81 + 3* | 33 + 3 | 18.3 + 0.9 | 316 + 56 | 0.3 + 0 | 0.1 + 0 | 56 + 2 |

Significantly different from the control group
*p < 0.05

TABLE 5

Effect of Saba ext. on peroxidation of salad oil

| Treatment (p.o) | Dose (mg/kg) | No. of rats | Triglyceride | Total protein | Alb. | A/G Ratio | F.F.A | β-Lipoprotein | HDL | Peroxidation |
|---|---|---|---|---|---|---|---|---|---|---|
| normal | | 7 | 28 + 4 | 6.9 ± 0.1 | 3.2 ± 0 | 0.84 ± 0.01 | 446 ± 29 | 78 ± 5 | 40 ± 2 | 8.9 ± 0.4 |
| Control | | 7 | 26 + 6 | 6.9 ± 0.1 | 3.1 ± 0 | 0.81 ± 0.01 | 578 ± 45 | 107 ± 6 | 33 ± 2 | 10.3 ± 0.6 |
| Saba ext. | 200 | 7 | 23 + 4 | 7.1 ± 0.1 | 3.2 ± 0.1 | 0.82 ± 0.02 | 516 ± 44 | 107 ± 8 | 38 ± 2 | 10.0 ± 0.3 |
| Saba ext. | 500 | 7 | 11 + 2 | 7.1 ± 0.1 | 3.1 ± 0 | 0.77 ± 0.02 | 480 ± 29* | 108 ± 4 | 35 ± 2 | 10.3 ± 0.8 |

Significantly different from the control group
< 0.05

EXAMPLE 6

FUNCTION FOR RELIEVING RHEUMATISM AND ARTHRITIS

Using the mackerel extract prepared in Example 1, the pharmaceutical function thereof on the Adjuvant Arthritis, which is the model experiment for inflammation including rheumatism and arthritis, was tested.

Test Method

Figure 7:
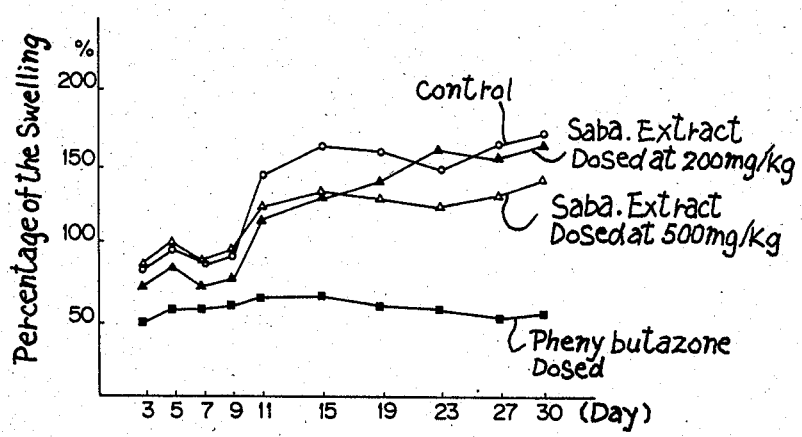
FIG. 7 is a graph showing the percentage of the swelling of the rats dosed with the mackerel extract prepared by the process of the invention and the percentage of the swelling of the rats which are not dosed with the extract.

The test was conducted generally in accordance with the Sele method. Using rats each having a body weight of 140 to 160 grams, 0.05 ml of a mixture of sterilized germ body of Mico-bacterium butyricum (DIFCO) in Bayol mixed in the ratio of 10 mg/ml was injected subcutaneously into the right paw of each rat and 0.05 ml of the same mixture was injected subcutaneously into the tail of each rat. The percentage of the swelling was obtained by measuring the volume of edemata growing on the paw and the tail of each rat. The results are shown in FIG. 7.

After the lapse of one month, the blood of each rat was picked out from the heart and subjected to hemological investigation. Degradation of bones of both legs were observed by means of X-ray photography. The extract was dosed to each rat of tested group one time a day through the mouth. The results of measurements are shown in Tables 6 and 7.

Test Results

By the subcutaneous injection, the right rear leg suffered a primary inflammation showing the peak inflammation on the fifth day after injection, and suffered a secondary inflammation beginning from the fifteenth day from the injection. The inflammation beginning from the fifteenth day from the injection was suppressed by addition of 500 mg/kg of the mackerel extract.

The inspection of the X-ray photographs revealed that the swelling of the edemata was also suppressed.

TABLE 6

Effect of Saba ext. on the serum in Adjuvant Rats

| Treatment (p.o.) | Dose (mg/kg) | No. of rats | GOT | GPT | ALP | Urea N | Cu |
|---|---|---|---|---|---|---|---|
| normal | | 7 | 126 ± 7 | 30 ± 3 | 23.0 ± 2.5 | 20 ± 2 | 152 ± 13 |
| control | | 10 | 118 ± 6 | 23 ± 3 | 23.1 ± 2.8 | 25 ± 2 | 207 ± 11 |
| Saba ext. | 200 | 10 | 117 ± 5 | 23 ± 2 | 19.3 ± 1.8 | 22 ± 1 | 214 ± 10 |
| Saba ext. | 500 | 10 | 127 ± 12 | 29 ± 7 | 19.5 ± 2.7 | 25 ± 3 | 217 ± 7 |
| Phenylbutazone | 50 | 7 | 118 ± 6 | 22 ± 2 | 16.4 ± 0.5 | 19 ± 2 | 193 ± 22 |

TABLE 7

Effect of Saba ext. on the serum in Adjuvant Rats

| Treatment (p.o.) | Dose (mg/kg) | No. of rats | Alb | $\alpha_1$-G | $\alpha_2$-G | $\beta$-G | $\gamma$-G | T.P. | A/G |
|---|---|---|---|---|---|---|---|---|---|
| normal | | 7 | 2.59 ± 0.2 | 0.84 ± 0.07 | 0.39 ± 0.03 | 0.83 ± 0.1 | 0.87 ± 0.1 | 5.8 ± 0.2 | 0.85 ± 0.1 |
| control | | 10 | 2.08 ± 0.08 | 1.37 ± 0.06 | 0.37 ± 0.06 | 0.88 ± 0.09 | 1.07 ± 0.14 | 5.8 ± 0.1 | 0.56 ± 0.03 |
| Saba ext. | 200 | 10 | 2.07 ± 0.16 | 1.09 ± 0.06 | 0.50 ± 0.04 | 0.89 ± 0.04 | 0.94 ± 0.09 | 5.7 ± 0.2 | 0.61 ± 0.06 |
| Saba ext. | 500 | 10 | 1.85 ± 0.18 | 1.28 ± 0.10 | 0.47 ± 0.06 | 0.95 ± 0.05 | 0.79 ± 0.04 | 5.4 ± 0.2 | 0.54 ± 0.07 |
| Phenylbutazone | 50 | 7 | 2.62 ± 0.22 | 0.94 ± 0.14 | 0.43 ± 0.04 | 0.88 ± 0.05 | 0.88 ± 0.11 | 5.8 ± 0.2 | 0.86 ± 0.13 |

In the foregoing description, the present invention has been specifically disclosed by referring to some examples thereof. However, it should be appreciated that various modifications and variations can be easily made by those skilled in the art without departing from the spirit of the invention. It is, thus, intended to include all such modifications and variations within the wide scope of the present invention defined by the appended claims.

What is claimed is:

1. A process for the preparation of fish and/or shellfish extracts, which comprises the steps of:
   (a) heating uncomminuted raw fish and/or shellfish to a temperature of not lower than 80° for 10 minutes to 1 hour to fully deactivate the autolysis enzymes contained in said fish and/or shellfish and simultaneously to remove fish smell;
   (b) adding a Bacillus subtilis derived proteinase of said fish and/or shellfish at a temperature of from 50 to 60° C. and at a pH of from 6.0 to 6.5 and decomposing for a period of 1 to 3 hours the proteins contained in said fish and/or shellfish to the stage of proteoses;
   (c) raising the temperature to not lower than 80° C. and maintaining at that temperature for 10 minutes to 1 hour to fully deactivate said Bacillus subtilis derived proteinase;
   (d) adding a Koji mould derived proteinase to said proteoses derived from said fish and/or shellfish at a temperature of from 40° to 50° C. and at a pH of from 6.0 to 7.0 and maintaining the mixture at said temperature for 1 to 3 hours to decompose said proteoses into peptides each having a molecular weight of substantially less than 3000 and free amino acids;
   (e) raising the temperature to not lower than 75° C. to fully deactivate said Koji mould derived proteinase; and
   (f) separating and then concentrating the resultant decomposition products, to produce fish and/or shellfish extracts.

2. A process as claimed in claim 1, wherein said fish and/or shellfish are selected from the group consisting of saurel, mackerel, sardine, mackerel pike, tuna, Atka mackerel, cod, cuttlefish, octopus, shrimp, prawn, oyster, corbicula, short-necked clam, hard-shelled mussel, species of ark shell, clam and mixtures thereof.

3. A fish and/or shellfish extract prepared by the process as claimed in claim 1, and including peptides each having a molecular weight of substantially less than 3000 and free amino acids, and not less than 50% by weight of crude proteins, and less than 1% by weight of crude fats.

* * * * *